(12) United States Patent
Heinz (10) Patent No.: US 9,033,937 B2
(45) Date of Patent: May 19, 2015

(54) SYRINGE

(71) Applicant: Transcoject GmbH, Neumünster (DE)

(72) Inventor: Jochen Heinz, Flintbek (DE)

(73) Assignee: Transcoject GmbH, Neumünster (DE)

( * ) Notice: Subject to any disclaimer, the term of this patent is extended or adjusted under 35 U.S.C. 154(b) by 0 days.

(21) Appl. No.: 13/969,671

(22) Filed: Aug. 19, 2013

(65) Prior Publication Data

US 2014/0052078 A1  Feb. 20, 2014

(30) Foreign Application Priority Data

Aug. 20, 2012  (DE) .......................... 10 2012 214 718

(51) Int. Cl.
*A61M 5/31* (2006.01)
*A61M 5/34* (2006.01)

(52) U.S. Cl.
CPC .............. *A61M 5/347* (2013.01); *A61M 5/3134* (2013.01)

(58) Field of Classification Search
CPC ..... A61M 5/3276; A61M 5/34; A61M 5/344; A61M 5/345; A61M 5/347; A61M 39/1011; A61M 2039/1033
USPC ........................... 604/206, 240–243, 533–535
See application file for complete search history.

(56) References Cited

U.S. PATENT DOCUMENTS

| | | | | |
|---|---|---|---|---|
| 5,403,288 A | * | 4/1995 | Stanners ....................... | 604/232 |
| 5,876,379 A | * | 3/1999 | Beauvais et al. .............. | 604/181 |
| 5,984,373 A | | 11/1999 | Fitoussi et al. | |
| 2004/0254538 A1 | * | 12/2004 | Murphy et al. ............... | 604/181 |
| 2006/0033334 A1 | | 2/2006 | Weber et al. | |
| 2007/0088283 A1 | * | 4/2007 | Hongo et al. ................. | 604/187 |
| 2007/0265577 A1 | * | 11/2007 | Uematsu et al. .............. | 604/200 |
| 2012/0116355 A1 | * | 5/2012 | Heinz et al. ................... | 604/535 |

FOREIGN PATENT DOCUMENTS

| | | |
|---|---|---|
| DE | 20 2004 012 714 U1 | 11/2004 |
| DE | 10 2009 019 340 A1 | 11/2010 |
| EP | 1 733 749 A1 | 12/2006 |
| WO | 89/09071 A1 | 10/1989 |
| WO | 2006/087763 A1 | 8/2006 |

\* cited by examiner

*Primary Examiner* — Nicholas Lucchesi
*Assistant Examiner* — Diva K Chander
(74) *Attorney, Agent, or Firm* — McGlew and Tuttle, P.C.

(57) ABSTRACT

A syringe with a syringe cylinder has a Luer-lock connection arranged at an axial end of the syringe cylinder. The Luer-lock connection includes a Luer cone and a rotatable threaded sleeve surrounding this. The rotatable threaded sleeve of the Luer-lock connection includes a radially outwardly directed prominence.

19 Claims, 7 Drawing Sheets

SYRINGE

CROSS REFERENCE TO RELATED APPLICATIONS

This application claims the benefit of priority under 35 U.S.C. §119 of German Patent Application DE 10 2012 214 718.7 filed Aug. 20, 2012, the entire contents of which are incorporated herein by reference.

FIELD OF THE INVENTION

The invention relates to a syringe, in particular to a medical syringe, with a syringe cylinder and with a Luer-lock connection which is arranged at an axial end of the syringe cylinder and which comprises a Luer cone and a rotatable threaded sleeve surrounding this.

BACKGROUND OF THE INVENTION

Syringes or medical syringes at their end as a rule comprise a Luer connection for the connection to a canulla or to a flexible tubing or likewise, which are to be connected. So-called Luer-lock connections are known, in order to secure this Luer connection, and these comprise an inner thread surrounding the Luer cone at a distance and screwed to the counter-connection. This on the one hand can be effected by way of rotation of the counter-connection, or however by way of rotating the thread, i.e. the threaded sleeve of the Luer-lock connection, for which the threaded sleeve is rotatably fastened on the Luer cone. The threaded sleeve however must be gripped on connecting, in order to rotate it. Thereby, there exists the danger that the fingers come into contact with the tip of the Luer cone itself, by which means regions which come into contact with the content of the syringe can become contaminated.

SUMMARY OF THE INVENTION

With regard to this state of the art, it is an object of the invention to improve a syringe, in particular a medical syringe with a Luer-lock connection comprising a rotatable threaded sleeve, to the extent that a good handling ability with a simultaneously reduced danger of contamination is given.

According to the invention a syringe is provided comprising a syringe cylinder and a Luer-lock connection arranged at an axial end of the syringe cylinder. The Luer-lock connection comprises a Luer cone and a rotatable threaded sleeve surrounding the Luer cone. The rotatable threaded sleeve comprises a radially outwardly directed prominence (projection, protuberance).

With regard to the syringe according to the invention, it is particularly the case of a medical syringe which for example can serve for receiving and preparing medication. The syringe in the known manner comprises a syringe cylinder, in which a movable plunger can be arranged. Moreover, in the known manner, a Luer-lock connection is arranged at an axial end of the syringe cylinder. I.e. the connection comprises a Luer cone and a sleeve which has an inner thread and which peripherally surrounds this connection. According to the invention, thereby one envisages the threaded sleeve being rotatable. I.e. the engagement of the thread in the threaded sleeve with the counter-piece to be fastened on the Luer cone is effected by way of rotation of the threaded sleeve relative to this counter piece. The counter-piece thereby, with a corresponding thread or prominence, engages into the thread of the threaded sleeve.

According to the invention, one envisages the rotatable threaded sleeve comprising a radially outwardly directed prominence. The prominence forms a grip region, on which the threaded sleeve can be gripped for its rotation. This prominence can be well gripped due to the fact that this prominence has a diameter which is enlarged compared to the diameter of the threaded sleeve. Moreover, the prominence provides a grip region which is remote from the tip of the Luer cone, since a radial distancing is given. Thus, the danger of the contact of the tip of the Luer cone on gripping the threaded sleeve is minimized. Moreover, the thus formed grip region on the outer periphery of the prominence, due to the greater diameter, has a better lever effect on rotating the threaded sleeve, which is advantageous if the threaded sleeve, as is described further below, is provided additionally with clamping means which fix the threaded sleeve after it has been tightened. A greater force is necessary for such a threaded sleeve for tightening, and this force can be mustered in a simpler manner via the grip region with a greater diameter which is formed by the prominence.

According to a first preferred embodiment of the invention, the radially outwardly directed prominence is arranged at the axial end of the threaded sleeve which faces the syringe cylinder. This arrangement has the advantage that the prominence is distanced in the axial direction as far as possible from the tip of the Luer cone. Thus, the danger of contact of the syringe of the Luer cone on gripping the threaded sleeve is further minimized. Moreover, the prominence can thus be supported on the axial end of the syringe cylinder also in the axial direction, so that a greater stability is given, and for example a breaking away of the prominence due to pressure in the axial direction can be prevented.

According to an alternative embodiment, it is however also possible for the radially outwardly directed prominence to be distanced in the axial direction from the axial end of the threaded sleeve which faces the syringe cylinder. Thereby, the prominence can be arranged on the axial end of the threaded sleeve which is away from the syringe cylinder or however also in an axial middle region between the two axial ends of the threaded sleeve. The axial distancing to the syringe cylinder can be advantageous in order to achieve a simpler rotatablity of the threaded sleeve, since the prominence of the threaded sleeve can thus be gripped more easily, without simultaneously firmly holding the syringe cylinder. A good compromise between an easy rotatablity and axial distance to the tip of the Luer cone can be achieved if the prominence is arranged in the axial middle region of the threaded sleeve.

The radially outwardly directed prominence at its radially outer end at all events has a greater radius than the threaded sleeve on its outer periphery. Preferably, the radius of the prominence from the middle axis of the syringe cylinder is at least so large, that it corresponds to half the radius of the syringe cylinder at its axial end. This axial end is the axial end which faces the Luer cone. With this radius, it is ensured that the prominence can be well gripped from the outside. Further preferably, the radius of the prominence from the middle axis of the syringe cylinder corresponds to at least two thirds of the radius of the syringe cylinder at its axial end. Thus, the prominence can be gripped even better and on its outer periphery has an even greater radial distance to the Luer cone. According to a particularly preferred embodiment of the invention, the radius of the prominence from the middle axis of the syringe cylinder corresponds at least to the radius of the syringe cylinder at its axial end. With this embodiment, the prominence can be particularly well gripped, since its outer periphery corresponds at least to the outer periphery of the syringe cylinder at its axial end which faces the Luer cone.

The radial or radially outwardly directed prominence is preferably designed in a disk-like manner. The disk-like prominence thereby further preferably has a circular shape and is arranged concentrically to the longitudinal axis or middle axis of the syringe cylinder. This is preferably also the axis, about which the threaded sleeve is rotatable. The prominence can be well gripped from all peripheral sides due to the disk-like design. Moreover, a large stability of the prominence is achieved and the base of the syringe cylinder, on which the Luer-lock connection is arranged, in the periphery of the Luer connection is preferably completely covered by the disk. The axial end of the syringe cylinder is simultaneously protected from damage by way of this.

Particularly preferably, the prominence extends in a disk-like manner parallel to a base of the syringe cylinder which surrounds the Luer cone. The disk-like prominence merges harmonically into the overall shaping of the syringe by way of this. As mentioned above, the base of the syringe cylinder is simultaneously covered and protected from damage by the disk.

According to a preferred embodiment, the disk-like prominence is designed in a closed manner. I.e. it completely covers the base of the syringe cylinder which surrounds the Luer cone and preferably has a closed surface. By way of this, one prevents contamination from being able to settle in the disk.

Alternatively, the disk-like prominence can also be designed such that it comprises one or more openings. Such openings can serve for minimizing the material requirement. Moreover, the openings or structuring in the disk-like prominence serve its fashioning. For example, arrows which mark the rotation direction can be designed as openings or recesses or deepenings in the disk-like prominence. Other markings such as indications as to the contents of the syringe, the manufacturer etc. can also be applied on the disk-like prominence in the form of openings or structuring.

Further preferably, the radial prominence has a radius which is greater than the radius of the syringe cylinder at its axial end. Preferably, the radial prominence projects radially at least slightly beyond the outer periphery of the base of the syringe cylinder. Thus, the prominence can be easily gripped on its outer periphery, without simultaneously gripping the syringe cylinder. Moreover, with a disk-like design of the prominence, the base of the syringe cylinder, which means the base at the end facing the Luer cone, is preferably completely covered and the disk-like prominence can be well gripped on the outer periphery of the syringe cylinder.

Preferably, the prominence can be structured on its outer periphery. This permits a good gripping ability and force transmission on rotation.

Moreover, the prominence in a further preferred embodiment can comprise an axially extending projection or collar, in a manner radially distanced to the threaded sleeve. The projection can be designed in the form of a thickening. The collar can preferably be designed in a sleeve-like manner. This means that the collar has a cylindrical shaping and preferably extends parallel to the longitudinal axis of the syringe cylinder or of the Luer cone. Thus, e.g. with a disk-like design of the prominence, the disk on the outer periphery can be thickened, so that an increased peripheral gripping surface is created, which renders it possible to grip and rotate the prominence on the outer periphery more easily. The axially extending projection can thereby extend away from the base of the syringe cylinder, i.e. extend essentially parallel to the longitudinal axis of the Luer cone. Alternatively or additionally, it can also extend in the opposite direction, for example by a certain amount parallel to the peripheral wall of the syringe cylinder and engage over this. Thus, an increased gripping surface is created at the outer periphery of the syringe cylinder. Preferably, a collar can extend from the prominence towards the cylinder in the axial direction, if the prominence is distanced in the axial direction to the axial end of the threaded sleeve which faces the syringe cylinder. Thus, the free space between the radial prominence and the base of the syringe cylinder is essentially peripherally closed by this collar. The collar thereby on the one hand forms an enlarged grip region, but on the other hand also prevents foreign bodies from being able to penetrate into the free space between the prominence and the syringe cylinder. Moreover, the collar or the projection can be supported on the base of the syringe cylinder in the axial direction, so that the prominence is supported given an axial pressure on the syringe cylinder. Preferably, a small distance remains between the projection or the collar and the base of the syringe cylinder, in order to ensure an easy rotatability of the threaded sleeve. This gap reduces with an axial pressure onto the radial prominence, until, in the extreme case, the collar can then come onto bearing contact on the axial end of the syringe cylinder.

Particularly preferably, the projection or collar is arranged on the outer periphery of the radial prominence. Thereby, it further preferably connects to the outer periphery of the syringe cylinder in the axial extension, which leads to an optically aesthetic design.

The threaded sleeve is rotatably fastened on the syringe cylinder, in particular on the Luer cone. For this, the threaded sleeve can comprise at least one inwardly directed projection, in particular a radially inwardly directed shoulder which engages into a groove on the foot of the Luer cone. Thus, the threaded sleeve is secured onto the Luer cone in the axial direction but is simultaneously rotatable. At least one friction means or clamping means can be arranged between the threaded sleeve and the Luer cone, in order to achieve a securing of the Luer-lock connection. A non-positive or positive fit engagement between the threaded sleeve and the foot of the Luer cone can be achieved by way of this, if the threaded sleeve is screwed to a counter-piece applied on the Luer cone. The threaded sleeve is prevented from inadvertently detaching again by way of this. This friction connection can be designed as is disclosed in German patent application DE 10 2009 019 340 (corresponding US Patent Publication US 2012116355 is hereby incorporated by reference in its entirety).

The invention is hereinafter described by way of example and by way of the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
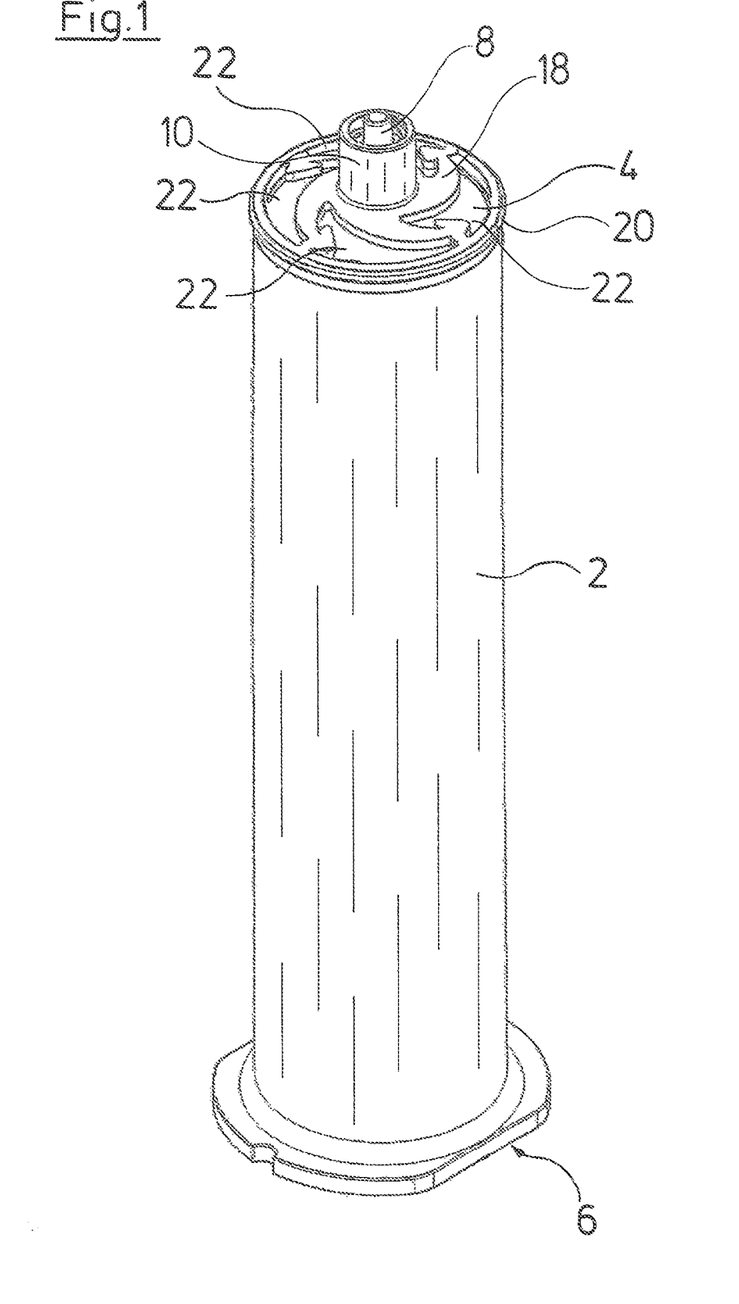
FIG. 1 is a perspective entire view of a syringe according to the invention.
Figure 3:
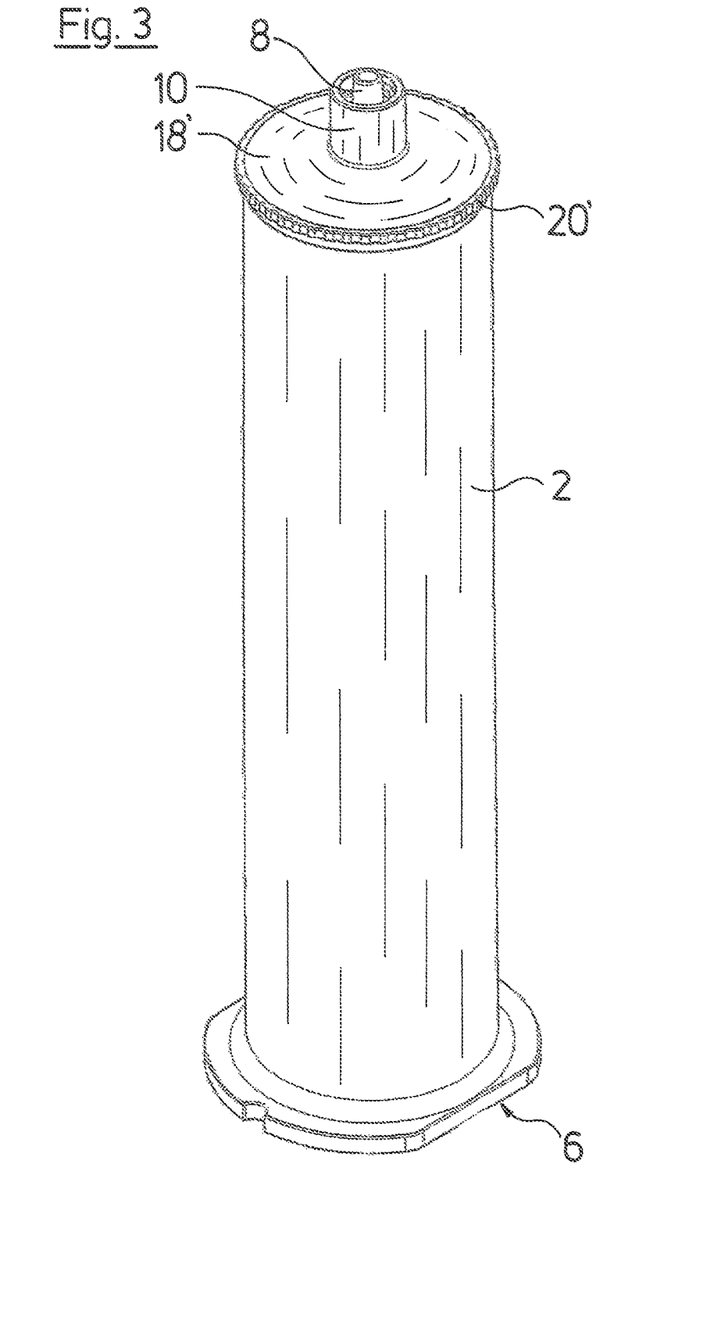
FIG. 3 is a perspective entire view of a syringe according to the second embodiment of the invention.
Figure 5:
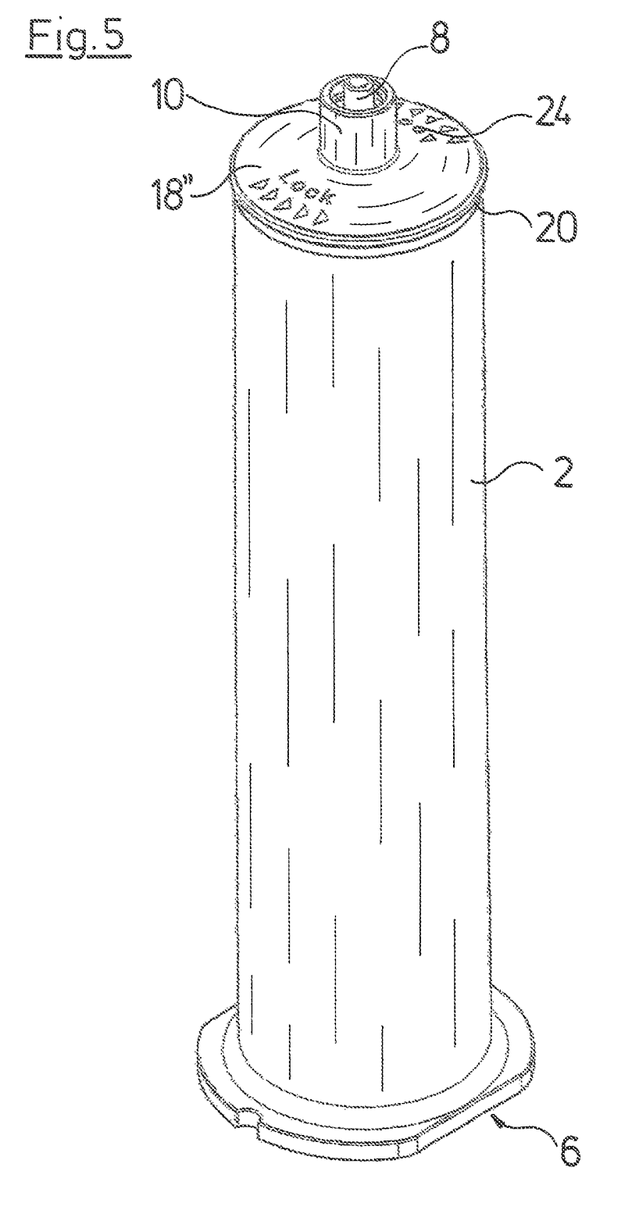
FIG. 5 is a perspective entire view of a syringe according to a third embodiment of the invention.

Referring to the drawings in particular, FIGS. 1, 3 and 5 in each case show only the syringe cylinder, the plunger is not recognizable in the figures.

The syringe shown in FIG. 1 according to a first embodiment of the invention, in a known manner comprises a syringe cylinder 2 which is closed by a base 4 at a first, front axial end and at the opposite second axial end 6 is designed in an open manner, wherein a plunger can be introduced through the second axial end 6 into the inside of the syringe cylinder 2 in the known manner. The base 4 comprises a central opening, on which a Luer cone 8 is formed. The Luer cone 8 in its inside comprises an opening extending into the inside of the syringe cylinder 2 and forms the entry and exit opening of the syringe. The Luer connection with the syringe according to the invention is designed as a Luer-lock connection. Thus, a threaded sleeve 10 is arranged around the Luer cone 8 in a radially distanced manner and, on its inner periphery in the known manner, comprises an inner thread 12 and on its foot away from the base 4 comprises a radially inwardly directed shoulder 14 which engages into an annular groove 16 on the foot of the Luer cone 8. Thus, the threaded sleeve 10 is secured on the Luer cone 8 in the axial direction X, but is rotatable about the longitudinal axis X relative to the Luer cone 8, in order to be screwed to a counter piece which is applied on the Luer cone 8 and which engages into the free space between the Luer cone 8 and the threaded sleeve 10, for the securement of this counter-piece.

According to the invention, the threaded sleeve 10 comprises a radially outwardly directed prominence 18. The prominence 18 is designed in an essentially disk-like manner and extends parallel to the base 4 of the syringe cylinder 2. Thereby, the disk-like prominence 18 with respect to the middle axis X has a slightly larger diameter than the syringe cylinder 2 at its base 4. The prominence 18 thus with its edge projects outwards beyond the outer periphery of the syringe cylinder 2 and thus forms a peripheral gripping surface 20, on which the prominence 18 and thus the threaded sleeve 10 can be gripped and rotated. This has the advantage that the threaded sleeve 10 does not have to be grasped in a region, in which there is the danger of the tip of the Luer cone 8 being touched and thereby contaminated. Moreover, thus a greater diameter for gripping the threaded sleeve 10 is provided, so that the threaded sleeve 10 can be rotated more easily. Moreover, the gripping surface 20 lies radially outside the outer periphery of the syringe cylinder 2, so that the syringe cylinder 2 also does not hinder the gripping and rotation of the threaded sleeve 10.

Figure 2:
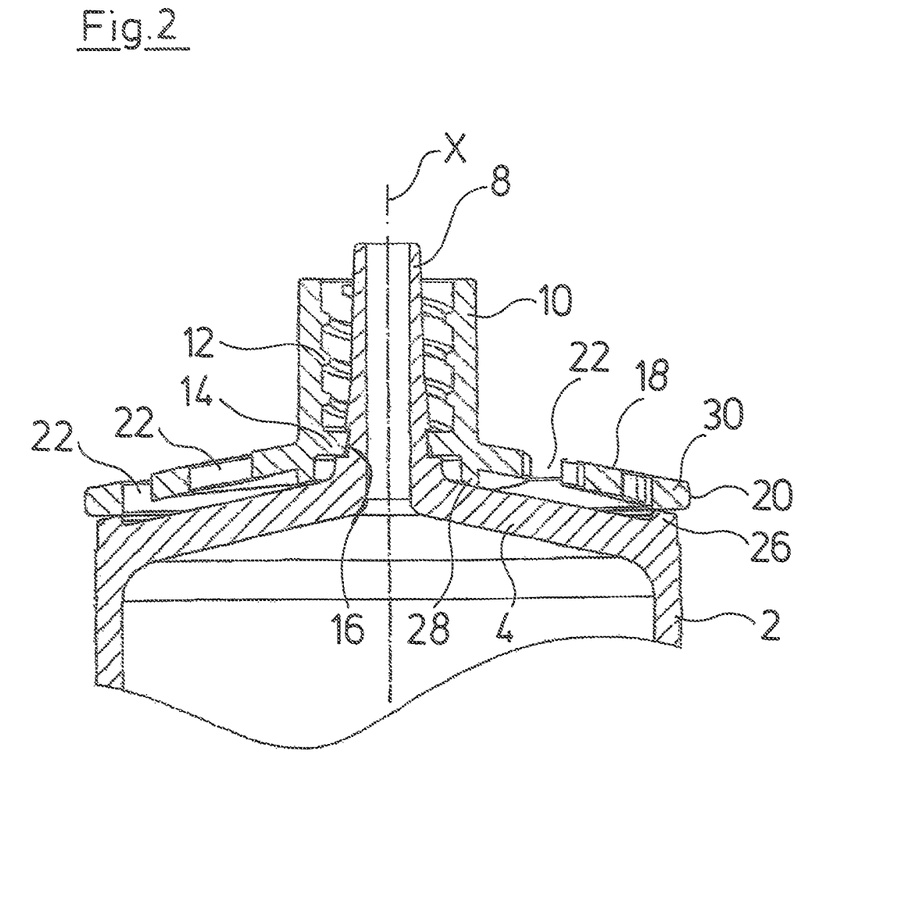
FIG. 2 is a sectioned view of the axial end of the syringe according to FIG. 1.

In the example shown in FIGS. 1 and 2, the prominence 18 is provided with openings 22 which, in this case, are shaped such that the remaining webs between the openings 22, as arrows, mark the rotation direction for the threaded sleeve 10.

Figure 4:
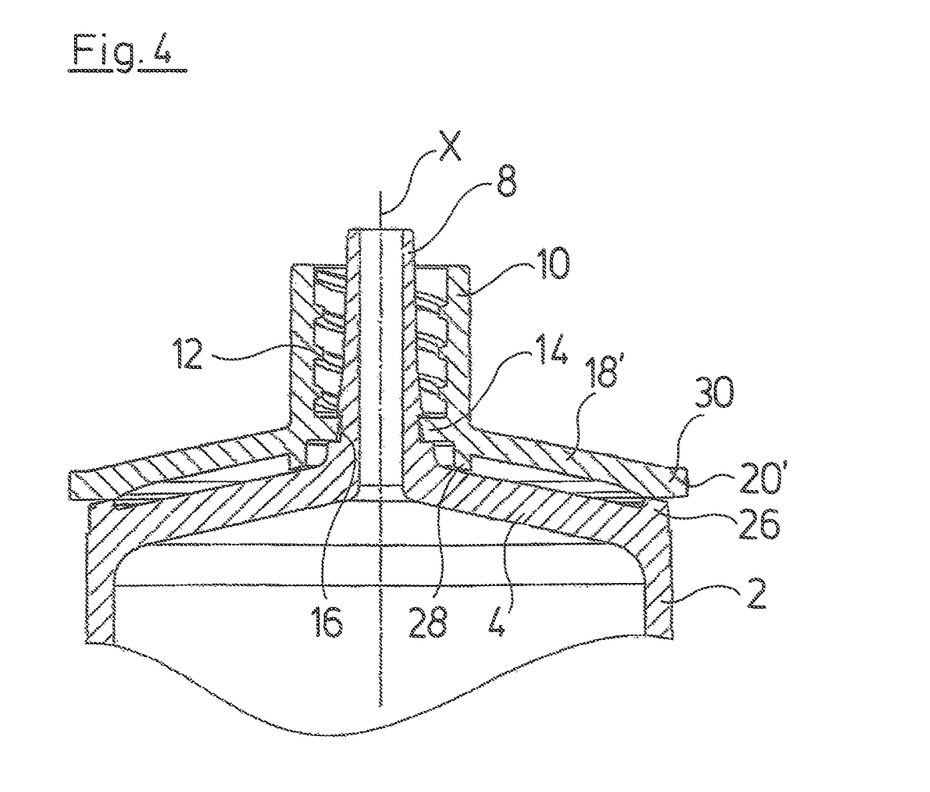
FIG. 4 is a sectioned view of the axial end of the syringe according to FIG. 3.

FIGS. 3 and 4 show a second embodiment example of the invention, which differs from the embodiment example explained by way of FIGS. 1 and 2 merely in the design of the prominence 18'. All remaining features are identical. With regard to the example shown in FIGS. 3 and 4, the prominence 18' is designed as a closed disk with closed surface. Thus, the prominence 18' completely covers the base 4 of the syringe cylinder 2. Moreover, the gripping surface 20' on the outer periphery of the prominence 18' in the example shown here is designed in a reeded manner, so that it permits a tighter grip. The third embodiment, which is shown in the FIGS. 5 and 6, differs from the two first embodiments in that the disk-like prominence 18" is designed in a closed manner, but is provided with an inscription 24 on the surface. Moreover, the gripping surface 20 with this embodiment in turn is designed in a smooth manner, but could also be designed in a structured or reeded manner, as is shown in FIG. 3.

With all three embodiment examples, the prominence 18, 18', 18" extends essentially parallel to the base 4 at the axial end of the syringe cylinder 2. Thereby, the prominence 18, 18', 18" does not lie on the base 4 in a surfaced manner, but is led in a manner distanced to this. Webs are provided for this, specifically a web 26 which extends in the axial direction X on the outer periphery of the base 4. Moreover, this is a web 28 which in the region of the inner periphery of the prominence 18, 18', 18" extends essentially in the extension region of the threaded sleeve 10 in the opposite direction to this, axially away from the prominence 18, 18', 18". The web 28 with its free end lies on the base 4. The free end of the web 26 bears on the prominence 18, 18', 18". Thereby, the prominence 18" in the region of its outer periphery comprises a thickening 30 which comes to lie on the web 26. In this manner, the prominence 18, 18', 18" is held in a manner distanced to the base 4 in the remaining regions, by which means the friction between the prominence 18, 18', 18" and the base 4 reduces. The thickening 30 on the outer periphery of the prominence 18, 18', 18" moreover has the advantage that the gripping surface 20, 20' is designed in a wider manner.

Figure 6:
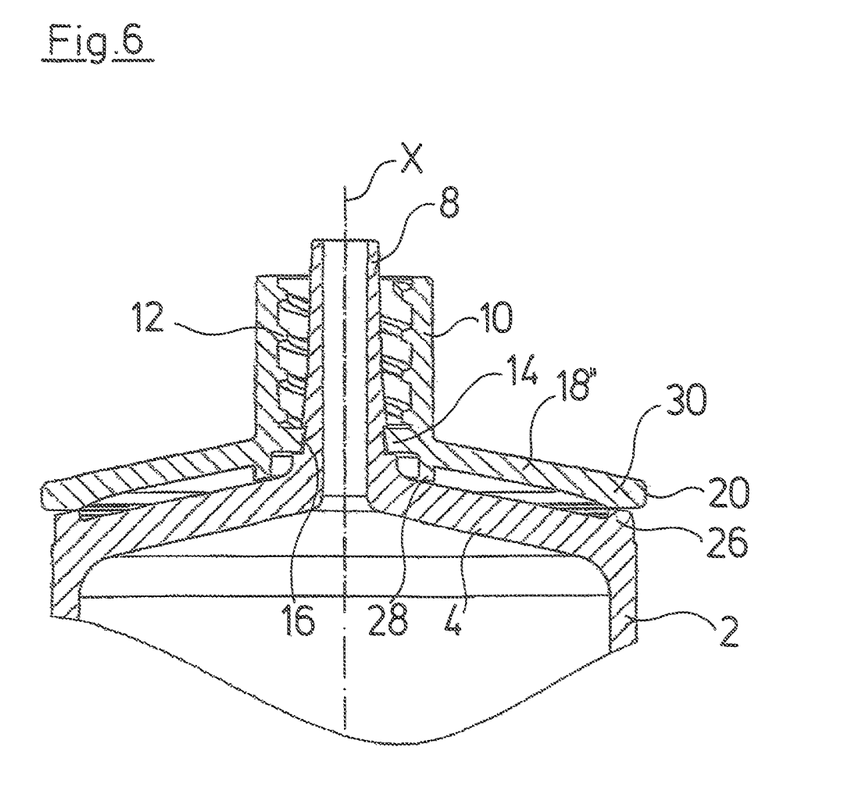
FIG. 6 is a sectioned view of the axial end of the syringe according to FIG. 5.
Figure 7:
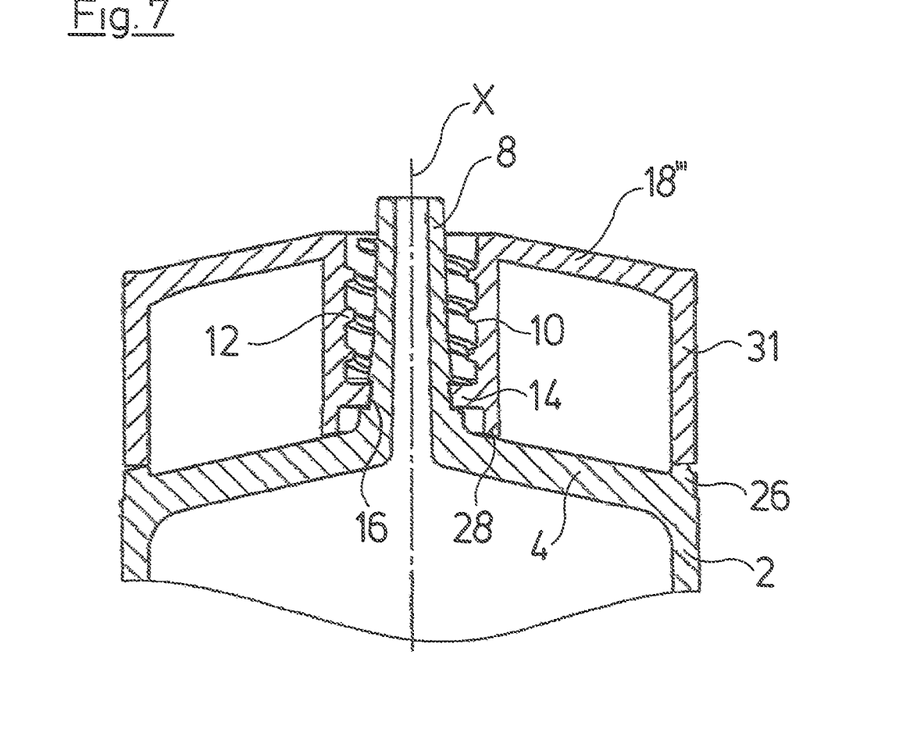
FIG. 7 is a sectioned view of the axial end of the syringe according to the invention, according to a fourth embodiment of the invention.

With the fourth embodiment of the invention which is shown in FIG. 7, the disk-like (disk or a disk portion) prominence 18'" in contrast to the third embodiment which is shown in FIG. 6, is not arranged on the axial end of the threaded sleeve 10 which faces the syringe cylinder 2, but at the opposite axial end of the threaded sleeve 10 which is away from the syringe cylinder 2. The disk-like prominence 18'" in this case is also fixedly connected to the threaded sleeve 10 as with the previous embodiments, specifically integrally formed with this as one piece. The disk-like prominence 18'" extends essentially parallel to the base 4 of the syringe cylinder 2. In this case too, the disk-like prominence 18' has a radius or diameter which is slightly larger than the outer radius of the syringe cylinder 2. A cylindrical collar 31 which extends from the prominence 18'" towards the syringe cylinder 2 is arranged on the outer periphery of the disk-like prominence 18'. The collar 31 has an outer diameter which corresponds essentially to the outer diameter of the syringe cylinder 2, so that it connects to this as an axial extension, in the axial direction. The cylindrical or peripheral collar 31 closes the free space 32 between the prominence 18'" and the base 4 of the syringe cylinder 2, at the outer periphery. By way of this, the collar 31 prevents foreign matter from being able to penetrate into the free space 32 and simultaneously provides an increased gripping surface on the outer periphery, so that the prominence 18'" can be gripped and rotated even more simply.

Moreover, with all four embodiments, friction or clamping means can be arranged between the shoulder 14 and the groove 16, for example by way of parts of the shoulder 14 or of the groove 16 being roughened. Here too, an eccentric arrangement between the shoulder 14 and groove 16 can be provided, in order given a rotation of the threaded sleeve 10, to achieve a clamping between the shoulder 14 and groove 16 when the counter-piece is inserted, in order to prevent the threaded sleeve 10 from releasing in an unintended manner.

While specific embodiments of the invention have been shown and described in detail to illustrate the application of the principles of the invention, it will be understood that the invention may be embodied otherwise without departing from such principles.

APPENDIX

List of Reference Numerals

2—syringe cylinder
4—base
6—second axial end
8—Luer cone
10—threaded sleeve
12—inner thread
14—shoulder
16—groove
18, 18', 18", 18'''—prominence
20, 20'—gripping surface
22—openings
24—inscription
26—web
28—web
30—thickening
31—collar
32—free space
X—longitudinal or middle axis

What is claimed is:

1. A syringe comprising:
a syringe cylinder; and
a Luer-lock connection arranged at an axial end of the syringe cylinder, the Luer-lock connection comprising a Luer cone and a rotatable threaded sleeve surrounding the Luer cone, the rotatable threaded sleeve comprising a radially outwardly directed prominence, wherein the threaded sleeve comprises at least one radially inwardly directed projection which engages into a groove on a foot of the Luer cone, said radially outwardly directed prominence having a disk shape forming a grip region for gripping said rotatable threaded sleeve such that the entire rotatable threaded sleeve rotates relative to said Luer cone.

2. A syringe according to claim 1, wherein the radially outwardly directed prominence is arranged at an axial end of the threaded sleeve which faces the syringe cylinder.

3. A syringe according to claim 1, wherein the radially outwardly directed prominence is distanced in an axial direction from an axial end of the threaded sleeve which faces the syringe cylinder.

4. A syringe according to claim 1, wherein a radius of the prominence from a middle axis of the syringe cylinder corresponds to at least half a radius of the syringe cylinder at a syringe cylinder axial end.

5. A syringe according to claim 1, wherein a radius of the prominence from a middle axis of the syringe cylinder corresponds to at least two thirds of a radius of the syringe cylinder at a syringe cylinder axial end.

6. A syringe according to claim 1, wherein a radius of the prominence from a middle axis of the syringe cylinder corresponds at least to a radius of the syringe cylinder at an axial end.

7. A syringe according to claim 1, wherein the prominence extends as a disk or a disk portion parallel to a base of the syringe cylinder, which surrounds the Luer cone.

8. A syringe according to claim 1, wherein the radially outwardly directed prominence that comprises a disk or disk portion is formed in a closed manner.

9. A syringe according to claim 1, wherein the radially outwardly directed prominence that comprises a disk or disk portion comprises one or more openings.

10. A syringe according to claim 1, wherein the radially outwardly directed prominence has a radius which is greater than a radius of the syringe cylinder at an axial end thereof.

11. A syringe according to claim 1, wherein the prominence is structured on an outer periphery, said prominence having an end portion, said end portion being located at one of a position located at said outer periphery and a position located beyond said outer periphery.

12. A syringe according to claim 1, wherein said threaded sleeve comprises a threaded sleeve portion, the prominence, in a region radially distanced to the threaded sleeve portion, comprising an axially extending projection or collar.

13. A syringe according to claim 1, further comprising a friction means or clamping means arranged between the threaded sleeve and the Luer cone.

14. A syringe comprising:
a syringe cylinder comprising a syringe cylinder outer periphery; and
a Luer-lock connection arranged at an axial end of the syringe cylinder, the Luer-lock connection comprising a Luer cone connected to the syringe cylinder and a rotatable threaded sleeve, the rotatable threaded sleeve comprising a sleeve portion having an inner thread surrounding the Luer cone and a radially outwardly directed prominence extending radially outwardly from the sleeve portion, said Luer cone comprising a Luer cone groove, said rotatable threaded sleeve comprising a rotatable threaded sleeve projection, said Luer cone groove receiving at least a portion of said rotatable threaded sleeve projection, said radially outwardly directed prominence extending to one of a position located at said syringe cylinder outer periphery and a position located beyond said syringe cylinder outer periphery, said Luer cone being in a fixed position, wherein said radially outwardly directed prominence and said sleeve portion are rotatable with respect to said Luer cone, said radially outwardly directed prominence being disk-shaped.

15. A syringe according to claim 14, wherein the radially outwardly directed prominence is arranged at an axial end of the threaded sleeve which axial end is adjacent to the syringe cylinder, wherein said rotatable threaded sleeve and said radially outwardly directed prominence are fixed in an axial position with respect to a longitudinal axis of said Luer cone, wherein said radially outwardly directed prominence and said rotatable threaded sleeve are only movable in a circumferential direction about said Luer cone.

16. A syringe according to claim 14, wherein the radially outwardly directed prominence is arranged at an axial end of the threaded sleeve which axial end is spaced a distance from the syringe cylinder, wherein the entire said rotatable threaded sleeve is rotatable with respect to said Luer cone.

17. A syringe according to claim 14, wherein the prominence has a maximum dimension in a direction extending radially outwardly that is greater than a maximum dimension of the syringe cylinder in the direction extending radially outwardly, wherein said prominence has a user grasping surface, said user grasping surface being located at a first distance from a longitudinal axis of said syringe cylinder, said syringe cylinder outer periphery being located at a second distance from said longitudinal axis of said syringe cylinder, said first distance being greater than said second distance.

18. A syringe according to claim 14, wherein the radially outwardly directed prominence comprises a disk or disk portion.

19. A syringe comprising:
a syringe cylinder comprising a syringe cylinder outer periphery; and
a Luer-lock connection arranged at an axial end of the syringe cylinder, the Luer-lock connection comprising a Luer cone connected to the syringe cylinder and a rotatable threaded sleeve, said rotatable threaded sleeve comprising a sleeve portion having an inner thread surrounding the Luer cone and a radially outwardly directed prominence extending radially outwardly from the sleeve portion, said radially outwardly directed prominence being integrally connected to said rotatable threaded sleeve, said Luer cone comprising a Luer cone groove, said rotatable threaded sleeve comprising a rotatable threaded sleeve projection, said Luer cone groove receiving at least a portion of said rotatable threaded sleeve projection, wherein said rotatable threaded sleeve is fixed in an axial direction of said syringe cylinder via said Luer cone groove and said rotatable threaded sleeve projection, said radially outwardly directed prominence comprising a user contact surface, said user contact surface and said radially outwardly directed prominence defining a means for gripping said threaded sleeve such said entire threaded sleeve is rotatable relative to said Luer cone, said user contact surface being located at a first distance from a longitudinal axis of said syringe cylinder, said outer periphery being located at a second distance from said longitudinal axis, said first distance being equal to or greater than said second distance.

* * * * *